(12) United States Patent
Free

(10) Patent No.: US 7,297,352 B1
(45) Date of Patent: Nov. 20, 2007

(54) COMPOSITIONS AND METHODS FOR THE TREATMENT OF FIBROMYALGIA

(75) Inventor: Elijah Free, Santa Cruz, CA (US)

(73) Assignee: Elijah Free, Santa Cruz, CA (US)

( * ) Notice: Subject to any disclaimer, the term of this patent is extended or adjusted under 35 U.S.C. 154(b) by 224 days.

(21) Appl. No.: 10/981,951

(22) Filed: Nov. 5, 2004

Related U.S. Application Data

(63) Continuation-in-part of application No. 10/973,334, filed on Oct. 25, 2004, now abandoned.

(51) Int. Cl.
*A61K 36/00* (2006.01)
(52) U.S. Cl. ...................................... 424/725
(58) Field of Classification Search ...................... None
See application file for complete search history.

(56) References Cited

U.S. PATENT DOCUMENTS

| 5,378,686 A | 1/1995 | Bennett |
| 6,210,738 B1 * | 4/2001 | Chen ........................... 426/597 |

OTHER PUBLICATIONS

Homan (Royal Pharmaceutical Society of Great Britain. Drug Preparation and Extraction (2002)).*

* cited by examiner

*Primary Examiner*—Susan Coe Hoffman
(74) *Attorney, Agent, or Firm*—Morrison & Foerster LLP

(57) ABSTRACT

The present invention relates to herbal compositions useful for the treatment of patients with diseases or disorders characterized by having a fibrotic component.

6 Claims, No Drawings

COMPOSITIONS AND METHODS FOR THE TREATMENT OF FIBROMYALGIA

RELATED APPLICATIONS

This application is a continuation-in-part of U.S. application Ser. No. 10/973,334, entitled "Compositions and Methods for the Treatment of Fibromyalgia," filed on Oct. 25, 2004 now abandoned, which is incorporated herein by reference in its entirety.

FIELD OF THE INVENTION

The present invention relates to the fields of treatment of diseases and disorders characterized by a fibrotic condition in the patient. This invention provides compositions of natural herbs for the treatment of these diseases and disorders as well as methods of synthesizing the herbal compositions and methods of using the herbal compositions to treat the diseases and disorders. A preferred use of the present invention is the treatment of fibromyalgia.

BACKGROUND OF THE INVENTION

Fibromyalgia is believed to be one of the most common causes of chronic pain that is suffered today. Accurate numbers, however, are quite difficult to determine because of the difficulty in diagnosing the disorder and because the experts often differ in how they define the disorder. This is in part due to the fact that Fibromyalgia is a syndrome rather than a disease. Diseases have known causes and work by well known mechanisms, while syndromes are defined by a patient having a set of signs or symptoms. Examples of other syndromes are rheumatoid arthritis and lupus. The risk of diagnosing patients by such methods is that patients with different diseases that should be treated by different approaches may be lumped into the same syndrome and some patients may not be diagnosed as having a syndrome when they are suffering from the same disorder. One common method of diagnosing fibromyalgia is by testing a patient experiencing chronic pain by applying firm pressure at eighteen specified "tender points." Patients with tenderness at eleven of such tender points are diagnosed as having fibromyalgia.

Due to the confusion in the field, there has been little progress toward development of a true cure because no single cause has been identified. There are various treatments that typically are designed to address the symptoms of fibromyalgia—the chronic pain—and the side effects brought on by the symptoms such as severe fatigue, insomnia, diarrhea, abdominal bloating, bladder irritation, headaches, etc., but no treatment has been developed that treats the underlying cause of fibromyalgia. However, true fibromyalgia, as it relates to the present invention, is caused by the build-up of fibrotic material in the soft tissue due to fibrin precipitation. This fibrin precipitation causes the chronic pain which in turn causes the side effects. Thus, there is a need for compositions and methods that treat the underlying cause of fibromyalgia by treating the condition that leads to the build up of fibrotic material.

In addition to fibromyalgia, several other disorders are characterized by a deposition of fibrotic material in the soft tissue. Thus a treatment that attacks the cause of fibromyalgia will also be effective in treating such other disorders. Thus there is a broader need for methods of treating diseases and disorders characterized by a fibrotic condition in a patient, especially fibromyalgia.

SUMMARY

The present invention addresses these long felt needs by providing herbal compositions for the treatment of such fibrotic conditions. In one embodiment, the herbal composition includes five herbs where each herb is selected from one of the following six groups of herbs; a first herb category consisting of White Pond Lilly Root, Greater Celandine, Cranes Bill Root, Black Haw, and Bladder Wrack, a second herb category consisting of Couch Grass, Burdock Root, Burdock Seed, Flaxseed, and Stinging Nettle, a third herb category consisting of Condurango Vine, Echinacea Root, and Pleurisy Root, a forth herb category consisting of Sheep Sorrel Herb, Black Walnut Leaves, Black Walnut Hulls, Black Walnut Green Hulls, Elecampane Root, and Cramp Bark, a fifth herb category consisting of from Elder Berries, Elder Flowers, and Hawthorn Berries, and a sixth herb category consisting of Lobelia Herb. In certain embodiments, the herbal mixture comprises only herbs from five of the herb categories and not the remaining herb category. In a preferred embodiment, the herbal composition includes at least five of the following six herbs in therapeutically effective amounts: White Pond Lilly Root, Couch Grass, Condurango Vine, Sheep Sorrel Herb, Elder Berries, and Lobelia Herb. In a more preferred embodiment, the herbal composition includes at least five of the following six herbs in the following ratios by weight: White Pond Lilly Root approximately 3 to 8 parts: Couch Grass approximately 1 to 5 parts: Condurango Vine approximately 1 to 5 parts: Sheep Sorrel Herb approximately 1 to 5 parts: Elder Berries approximately $\frac{1}{2}$ to 4 parts: Lobelia Herb approximately $\frac{1}{4}$ to 3 part. In a yet more preferred embodiment, the herbal composition includes at least five of the following six the herbs in the following ratios by weight: White Pond Lilly Root approximately 5 parts: Couch Grass approximately 3 parts: Condurango Vine approximately 3 parts: Sheep Sorrel Herb approximately 3 parts: Elder Berries approximately 2 parts: Lobelia Herb approximately 1 part. In certain variations of the above embodiments, the herbal mixture comprises only five of the herbs and not the remaining herb.

In certain embodiments, the herbal composition may be delivered as a dry mixture, for example in a capsule or compressed tablet. In other embodiments, the mixture is a liquid, for example a syrup, an herbal tincture, or a tea. In another embodiment, the mixture is in a decoction. Preferred herbal tinctures are alcohol or alcohol:water solutions. More preferred herbal tinctures include glycerin.

Another aspect of the present invention includes methods of making any of the above herbal compositions. In one embodiment, the herbal composition is made by mixing the dried herbs into a homogenous mixture. The homogenous mixture in certain embodiments may be further compressed into a tablet with other appropriate adjuvants to effect therapeutic delivery or loaded into a capsule. In another embodiment, the herbal composition is extracted with an alcohol or alcohol:water solution to create a tincture. In one variation, the herbs are mixed together and then extracted. In another variation, the herbs are extracted separately and then the extract liquids are mixed. In certain variants, the extract liquids may be further separated from the insoluble herbal components.

Yet another aspect of the present invention includes use of any of the above herbal compositions for treatment of a fibrotic condition. In preferred embodiments, the fibrotic conditions may be one of the following: cystic fibrosis, liver fibrosis, idiopathic pulmonary disease (pulmonary fibrosis), progressive systemic sclerosis (scleroderma), mixed connective tissue disease (MCTD), inclusion body myositis (IBM), chronic restrictive pericarditis, fibrous breast tissue (fibrocystic disease), fibroadenomas, fibroid tumors, endometriosis, retroperitoneal fibrosis, congenital fibrous ankylosis of multiple joints (AMC), acute disseminated intravascular coagulation (DIC), cataracts and fibrous eye conditions, and fibrosarcomas. In a more preferred embodiment, the fibrotic condition is fibromyalgia. The methods of treatment include administering any of the above herbal compositions in a therapeutically effective dose. In certain embodiments, the herbal composition is delivered three times per day.

DETAILED DESCRIPTION OF THE PREFERRED EMBODIMENTS

The herbal mixtures of the present invention may be used to treat a wide range of fibrotic conditions. The herbal mixtures address the underlying metabolic imbalance that leads to the precipitation of fibrin in fibrotic conditions. The precipitated fibrin, depending upon the nature of the fibrotic condition, leads to a host of symptoms associated with each respective disorder.

The medical community groups a number of ailments that may or may not be related in terms of the actual cause of the particular ailments. Historically, the medical community has classified ailments by symptomology, thus aliments with similar symptoms are considered to be in the same family of disease. Such classifications are termed syndromes such as fibromyalgia or lupus. As discussed in the background, fibromyalgia is defined by its symptomology, i.e., experiencing tenderness at eleven of eighteen tender points throughout the body. However, for the purposes of this invention, such grouping of ailments fails. Ailments that share a common symptomology or common medical terminology or name may not necessarily be related at all with respect to treatment with the herbal mixtures of the present invention. For example, ailments that share the medical nomenclature of fibrous, fibrotic, etc. may not be related by the same actual metabolic cause.

The herbal compositions of the present invention are designed to treat the metabolic cause of a series of related ailments which are related by having a similar metabolic cause. Specifically, the herbal compositions treat fibrotic conditions. For the purposes of the present invention, "fibrotic conditions" shall mean those diseases and conditions that share a similar metabolic cause. Fibrotic conditions include the following ailments: cystic fibrosis, liver fibrosis, idiopathic pulmonary disease (pulmonary fibrosis), progressive systemic sclerosis (scleroderma), mixed connective tissue disease (MCTD), inclusion body myositis (IBM), chronic restrictive pericarditis, fibrous breast tissue (fibrocystic disease), fibroadenomas, fibroid tumors, endometriosis, retroperitoneal fibrosis, congenital fibrous ankylosis of multiple joints (AMC), acute disseminated intravascular coagulation (DIC), cataracts and fibrous eye conditions, fibrosarcomas, and fibromyalgia. A preferred fibrotic condition to be treated with the herbal compositions of the present invention is fibromyalgia.

While not wanting to be limited by the theory of action of the herbal compositions, the herbal compositions function by addressing a nutritional deficiency. The metabolic cause of the fibrotic conditions alluded to above is a complicated one. The body needs to maintain a certain amount of fibrin, but in a state of semi-solvency. When there is this specific nutritional deficiency, then the fibrin, which should remain in its semi-dissolved state, precipitates or becomes hardened, and begins to grow along the soft tissue just like the roots of a plant. As a result, the soft tissue becomes less elastic until it becomes rigid, literally anchored to other tissue, resulting in pulling, resistance, and eventually pain. True fibrotic tissue is strands of fascia (soft tissue) that has become hardened and painful. It is most common on the hips, shoulders, buttocks and thighs. It may, however be also present in other parts of the body.

The herbal compositions of the present invention do not directly affect the hardened fibrotic tissue at all. Rather, the specific nutritional deficiency that leads to the hardening of the fibrin is addressed through the herbal compositions. The herbal compositions restore the natural metabolism and chemistry of the body by providing the body with the needed missing nutrients. With the metabolism restored to the correct balance, the body is able, on its own, to begin to re-absorb back the extraneous precipitated or hardened fibrotic tissue. This fibrotic tissue, over a period of time, literally vanishes as the affected tissue returns to its normal consistency—flexible, free-flowing, and pain-free.

Thus the direct therapeutic action of the herbal mixture is strictly nutritional in activity. The specific nutritional deficiency is directly addressed. Through this action, the body's chemistry is restored back to its original metabolic balance. As this is achieved, the body is then able to re-absorb back the hardened fibrotic tissue on its own. Thus, as discussed above, the herbal mixture is useful for treatment of a range of fibrotic conditions which are characterized by a similar metabolic cause.

Typically, within the first three to four weeks of treatment, there will be a change in the consistency of the tissue nearest the surface of the skin indicating that the process has begun. Over a period of months, there will be a continuous softening to the hardened tissue. Pain relief will begin after the formulas have been properly taken on a regular basis.

As mentioned to in the background, the definition of fibromyalgia that is used in the medical community today does not work for the present invention because the current methods of diagnosing fibromyalgia may include patients that are experiencing chronic pain that is not due to the fibrotic tissue such as patients who are suffering from Lyme's disease or have suffered physical trauma and may not include other patients who do have the fibrotic tissue. For example, a patient who experiences tenderness at only two of the tender points may still have fibrotic material built up at those points and still therefore be considered as suffering from fibromyalgia for the purposes of treatment by the herbal compositions of the present invention. Therefore, fibromyalgia shall mean a condition wherein there is a build-up of hardened fibrinous tissue that causes pain, discomfort, pulling and a barrier to leading a pain-free and normal life. This fibrinous tissue has heretofore, before this invention, been literally impossible to alleviate or cause to lessen in any way at all, even to the smallest degree. The patient who has true Fibromyalgia possesses an over-abundance of hardened fibrinous tissue. The definition of over-abundant fibrinous tissue is wherein there exists this specific type of tissue more abundant than in the norm, even to a small degree. If this specific fibrinous tissue is not present in any type of varying degree, then it shall be understood that the patient does not have Fibromyalgia and is suffering from some other condition or syndrome.

Methods of Preparing the Herbal Compositions

The herbal compositions of the present invention may be made by any method available to one of skill in the art. The preferred herbal composition comprises White Pond Lilly Root, Couch Grass, Condurango Vine, Sheep Sorrel Herb, Elder Berries, and Lobelia Herb. In a more preferred embodiment, the herbal composition is mixed at the following ratios by weight: White Pond Lilly Root approximately 3 to 8 parts: Couch Grass approximately 1 to 5 parts: Condurango Vine approximately 1 to 5 parts: Sheep Sorrel Herb approximately 1 to 5 parts: Elder Berries approximately ½ to 4 parts: Lobelia Herb approximately ¼ to 3 part. In a yet more preferred embodiment, the herbal composition is mixed at the following ratios by weight: White Pond Lilly Root approximately 5 parts: Couch Grass approximately 3 parts: Condurango Vine approximately 3 parts: Sheep Sorrel Herb approximately 3 parts: Elder Berries approximately 2 parts: Lobelia Herb approximately 1 part.

The herbs used to make the herbal mixture may be obtained from any available source. Examples of available sources include Blessed Herbs, StarWest Botanicals, and Pacific Botanicals. In a preferred embodiment, the herbs used to make the herbal mixture are dried, raw herbs. Dried, raw herbs may be obtained from reputable supplier of herbs. The preferred herbs are organic herbs, more preferred are wild crafted herbs.

The herbal mixture may be prepared for use in any form of delivery that can deliver a therapeutically effective dose. Preferred examples are as an herbal tincture, either alcoholic or a water-alcohol mix or a water-alcohol-glycerin mix, as a syrup, as a tea, as a decoction, or as a homogenized mixture of the dried herbs. For convenience, the homogenized mixture of dry herbs may be packaged in a capsule or compressed into a tablet. The herbal tincture may be delivered as a liquid supplement or delivered in a capsule.

Herbal tinctures may be prepared by any of a number of commonly available procedures used in the art. Tinctures may be prepared using classic methods of herbology as well as using modern technology designed for chemical or pharmaceutical processing. Modern technology may be used to improve the precision and reduce the labor required to make the herbal compositions. The herbs may be mixed together before extraction with the alcohol or alcohol:water mix or alcohol:water:glycerin mix. Alternatively, the herbs may be extracted individually and then mixed together.

The preferred extraction method is to mix the dry herbs together and then extract together. In an alternate embodiment, the dry herbs may be extracted individually and then combine the extracts. In a preferred embodiment, any of the herbal mixture compositions described above may be measured into alcohol or water:alcohol or water:alcohol:glycerin solution. In a more preferred embodiment, one pound of the dry herbal mixture is combined with between one and one half liters and two and one half liters of eighty proof alcohol. In a yet more preferred embodiment, between two and ten ounces of glycerin may be added to the extraction mix.

Once the herbs have been added to solution for extraction, it is preferred that the herbs are allowed to extract for ten to fifteen days. The herbs may be extracted for a longer period, but in general the tincture will not gain further potency. Once the herbs have extracted for a time sufficient for the tincture to achieve therapeutically effective potency, it is preferred that the insoluble components are removed from the tincture. Any method of separation may be used. By way of example, but not limitation, a press may be used to separate the soluble and insoluble components and the mix may be further strained through a material such as cheese cloth. Once completed, the tincture may then be stored as needed.

Methods of Using the Herbal Compositions

The methods of using the herbal compositions will vary depending upon the nature of the herbal composition. One of skill in the art can easily determine the appropriate dosage regimen based upon routine techniques in the art. Dosages will depend upon the form of the herbal composition—tincture, dried mix, etc. The dosages will also depend upon how potent the herbs are that are used in the herbal composition. For example, one of skill in the art would recognize that wild herbs tend to be stronger than cultivated herbs and adjust accordingly. A preferred dosage regimen is to deliver the herbal composition three times daily to spread the delivery of the nutrients throughout the day. The preferred time for delivery is between meals or five to ten minutes before meals.

A preferred method of delivery is to apply an herbal tincture directly to the mouth to allow absorption through the mucus membrane of the mouth. However, delivery of the tincture or dry herbal mixture in a capsule or tablet that is broken down in the digestive tract will still function. One of skill in the art would have no difficulty in adjusting the dosage regimen accordingly.

Once a patient begins to take the herbal composition, their body will begin to absorb the hardened fibrotic material in the soft tissue very quickly. However, since the herbal composition relies on the body's natural metabolism to operate in this manner, the time for the herbal composition to take effect will vary from person to person. In general, the herbal compositions must be applied for three to four weeks before results will be noticeable.

The re-absorption process will increase as more tissue is reabsorbed and restored back to its natural state. However, it is preferred that the application of the herbal composition continue until all symptoms have disappeared. The average time to effect such complete disappearance of symptoms will vary from patient to patient. Typically at least ten months to a year are needed. However, depending upon the severity of the case and how long each person may have had the nutritional deficiency, treatment may need to continue for a longer period.

After all of the tissue had been restored to normal, it is preferred that the patient continues with the determined dosage for at least another three months. Then the dosage regimen may be tapered off gradually thereafter. For example, the dosage may be lessened to two times a day and then eventually to once a day if all symptoms of fibromyaligia do not return.

EXAMPLE

Preparation of the Herbal Composition as a Tincture

The raw, dried herbs were purchased from a reputable supplier of herbs. Each herb was carefully measured according to the following ratios by weight:

| | |
|---|---|
| White Pond Lilly Root | 5 parts |
| Couch Grass | 3 parts |
| Condurango Vine | 3 parts |
| Sheep Sorrel Herb | 3 parts |
| Elder Berries | 2 parts |
| Lobelia Herb | 1 part |

Each measured herb was placed into a holding bag. Once all the herbs had been weighed out, the herbs were mixed until adequately homogenized together.

Exactly one pound of dry herbal mix was measured out into a one gallon glass jar. Then one and three quarters liter of eighty proof vodka was poured onto the mixture. Then exactly six ounces of pure vegetable glycerin was added. The lid was tightly screwed on, and then the entire bottle containing the mixture was shaken well.

The mixture within the bottle was placed in a cool dark place for exactly fifteen days. After that, the mixture was placed in a press that gives ten tons of cold pressure and was squeezed out so that the extracted liquid was separated from the bulk herb. The pressed out remaining bulk was discarded. The resultant liquid was strained through cheese cloth, bottled and stored.

Use of the Herbal Tincture

The herbal tincture was provided to patients with fibromyalgia. The patients took one half of one eyedropper three times daily between meals (approximately 0.75 mL). The patients were further advised to drink a glass of water.

The herbal mixture was used to treat about twenty four patients. All of the patients were women. The age of the patients in the study was from late thirties to early sixties. The herbal mixture displayed no difference in efficacy of treatment based upon the age of the patient. More than half of the patients were overweight with several running towards obesity. Again, there was no difference in efficacy based upon the weight of the patient.

The average time that it took for the first signs of tissue softening to be evident was between three to four weeks. The one week difference was considered to be negligible. All the patients displayed a similar softening of the tissue.

The pain levels reported by the patients at the beginning of treatment ranged from five all the way to ten depending upon the severity of the fibrosis of the tissue. The factors considered were density of affected tissue, the length of time that the problem was manifest to the person, where the tissue was located, how much the tissue limited daily and extra-curricular activities.

The first patient treated with the herbal tincture was reported a pain level of ten level. She had been aware of the abnormality of the tissue for twenty years. The fibromyaligia tissue was primarily located in the soft tissue of her body. There was a noted difference in the tissue after only two weeks of usage. Over the next ten months, ranging from the beginning of November of 2003 to the middle of September of 2004, the pain reported by the patient has gone from a ten to a zero. The patient determines the amount of pain that they are experiencing based on the qualitative value of pain that they have previously experienced before the advent of Fibromyalgia. The patient is requested to base their answer on a scale from zero to ten with ten being the most intense pain and zero being pain free. All facets of her life that had previously been affected by the fibromyalgia tissue have been restored back to normal. The other patients who have continued the treatment with the herbal tincture have experienced similar reduction in pain and softening of the fibrotic tissue.

I claim:

1. An herbal composition comprising White Pond Lilly Root, Couch Grass, Condurango Vine, Sheep Sorrel Herb, Elder Berries.

2. The herbal composition of claim 1, wherein the herbs are in a dry mixture.

3. The herbal composition of claim 1, wherein the herbs are in a tincture.

4. The herbal composition of claim 3, wherein the tincture is an alcohol:water mix.

5. The herbal composition of claim 4, wherein the tincture further comprises glycerin.

6. The herbal composition of claim 1, wherein the herbs are in a decoction or a tea.

* * * * *